(12) United States Patent
Clement et al.

(10) Patent No.: US 7,993,685 B2
(45) Date of Patent: Aug. 9, 2011

(54) BRANCHED-CHAIN AMINO ACID COMPOSITION FOR IMPROVING SKELETAL MUSCLE PROTEIN METABOLISM

(75) Inventors: Ken Clement, Oakville (CA); Shan Chaudhuri, Oakville (CA); Phil Apong, Oakville (CA); Michele Molino, Oakville (CA); Jason Peters, Oakville (CA)

(73) Assignee: Northern Innovations and Formulations Corp., Oakdale (CA)

( * ) Notice: Subject to any disclaimer, the term of this patent is extended or adjusted under 35 U.S.C. 154(b) by 0 days.

(21) Appl. No.: 12/928,481

(22) Filed: Dec. 13, 2010

(65) Prior Publication Data

US 2011/0092587 A1    Apr. 21, 2011

Related U.S. Application Data

(62) Division of application No. 11/745,859, filed on May 8, 2007, now abandoned.

(51) Int. Cl.
*A61K 36/00* (2006.01)
(52) U.S. Cl. ........................................... 424/725
(58) Field of Classification Search ................... None
See application file for complete search history.

*Primary Examiner* — Qiuwen Mi

(57) ABSTRACT

The present invention relates to compositions and methods for improving skeletal muscle protein metabolism through encouraging skeletal muscle protein synthesis, reducing skeletal muscle protein degradation, and attenuating inflammatory signaling in exercising muscle.

8 Claims, No Drawings

BRANCHED-CHAIN AMINO ACID COMPOSITION FOR IMPROVING SKELETAL MUSCLE PROTEIN METABOLISM

RELATED APPLICATIONS

This application is a divisional of and claims the benefit of priority of U.S. patent application Ser. No. 11/745,859, filed on May 8, 2007 (now abandoned), the disclosure of which is hereby fully incorporated by reference.

FIELD OF THE INVENTION

The present invention relates to a nutritional composition for improving the protein metabolism of skeletal muscles. A method of the same is also provided.

BACKGROUND OF THE INVENTION

Body composition, including muscle, is influenced both by genetic factors and environmental stimuli. Genetic factors are typically difficult, if not impossible to alter through intervention. Environmental factors however are routinely manipulated and important environmental factors that effect muscle metabolism, such as food intake and exercise, effect muscle metabolism within hours of stimulation A Gene and protein expression patterns change in response to these stimuli. These changes result in muscle adaptations such as muscle atrophy (loss) via muscle protein catabolism (breakdown) or muscle hypertrophy (increase) via muscle protein accretion. These opposing actions are not mutually exclusive and the determination of muscle loss or gain is the net effect of both positive and negative factors governing muscle development.

Exercise is a major stimulus of skeletal muscle growth. During several hours post-exercise there are dynamic changes in the rates of both skeletal muscle synthesis and breakdown. The consumption of specific dietary components is known to further influence the response of skeletal muscle to exercise. The main component of food that is known to stimulate increased muscle protein synthesis is amino acids (Rennie M J. Body maintenance and repair: how food and exercise keep the musculoskeletal system in good shape. Exp Physiol. 2005 July; 90(4):427-36). Increased levels of circulating essential amino acids have been shown to stimulate protein synthesis (Smith K, Reynolds N, Downie S, Patel A, Rennie M J. Effects of flooding amino acids on incorporation of labeled amino acids into human muscle protein. Am J Physiol. 1998 July; 275(1 Pt 1):E73-8).

Exercise stimulates inflammatory pathways which contribute to anabolic responses. However, excessive activation of inflammatory signaling molecules such as Nuclear Factor kappa B (NF-κB) has been implicated in several disease states involving loss or weakening of muscle (Kramer H F, Goodyear L J. Exercise, MAPK, and NF-{kappa}B Signaling in Skeletal Muscle. J Appl Physiol. 2007 Feb. 15). In these situations skeletal muscle protein breakdown exceeds protein synthesis.

It would therefore be advantageous for an individual concerned with maintaining or increasing lean skeletal muscle mass to consume a nutritional composition directed at improving skeletal muscle metabolism, to encourage skeletal muscle protein synthesis while minimizing skeletal muscle protein breakdown.

SUMMARY OF THE INVENTION

The foregoing needs and other needs and objectives that will become apparent for the following description are achieved in the present invention, which comprises one or more branched-chain amino acids or derivatives thereof, a plant extract for attenuating NF-κB signaling, and γ-butyrobetaine or derivative thereof for inducing vasodilation. Administration of the composition of present invention provides a method for improving the skeletal muscle protein metabolism of an individual.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards improving skeletal muscle protein metabolism, both in terms of promoting increased muscle protein accrual via increased protein synthesis and in terms of reducing the breakdown of skeletal muscle protein. The present invention is particularly useful for individuals engaged in regular intense physical activity who wish to gain lean muscle mass and size or minimize muscle loss.

In an embodiment of the present invention, a nutritional composition comprised of BCAAs is provided. The BCAAs employed may be selected from Leucine, Isoleucine and Valine or derivatives of each thereof.

In an embodiment of the present invention, a nutritional composition comprised of BCAAs and at least one ingredient known to attenuate NF-κB signaling is provided. In a preferred embodiment the ingredient known to attenuate NF-κB signaling is an extract of *Andrographis paniculata*.

In an embodiment of the present invention, a nutritional composition comprised of BCAAs, at least one ingredient known to attenuate NF-κB signaling and at least one ingredient known to increase vasodilation via increased levels of nitric oxide is provided. In a preferred embodiment the ingredient known to increase vasodilation via increased levels of nitric oxide is γ-butyrobetaine or derivatives thereof.

In a preferred embodiment of the present invention, a nutritional composition comprised of Leucine, Isoleucine and Valine or derivatives of each thereof, an extract of *Andrographis paniculata* and γ-butyrobetaine or derivatives thereof is provided for improving skeletal muscle protein metabolism.

Branched-Chain Amino Acids

The branched-chain amino acids (BCAAs) consist of Leucine, Isoleucine and Valine. BCAAs are considered essential since humans cannot synthesis them—they must be obtained from the diet—despite their importance. They are not only used in the synthesis of other amino acids but are important in the regulation of the anabolic process in skeletal muscle. BCAAs not only increase the rate of protein synthesis but also inhibit protein degradation (Matthews D E. Observations of branched-chain amino acid administration in humans. J Nutr. 2005 June; 135(6 Suppl):1580S-4S).

In various embodiment of the present invention detailed in examples 1 and 2 below, the nutritional supplement comprises BCAAs or derivatives thereof. The amount of BCAAs or derivatives thereof in a serving of the nutritional supplement is from about 0.7 g to about 10.5 g.

The preferred embodiment of the present invention comprises the BCAAs Leucine, Isoleucine and Valine or derivatives of each thereof in the following amounts. A serving of the nutritional supplement comprises Leucine or derivatives thereof from about 0.5 g to about 8.0 g. A serving of the nutritional supplement comprises Isoleucine or derivatives thereof from about 0.07 g to about 3.0 g. A serving of the nutritional supplement comprises Valine or derivatives thereof from about 0.1 g to about 3.5 g. Furthermore, in the preferred embodiment of the present invention, the ratio of Isoleucine to Leucine to Valine in the nutritional composition is about 1 to 2.3 to 1.2.

*Andrographis paniculata*

*Andrographis paniculata* is a medicinal herb used traditionally throughout Asia used to treat a number of conditions. One of the active ingredients of *Andrographis paniculata* extract is the diterpene, andrographolide. (Shen Y C, Chen C F, Chiou W F. Andrographolide prevents oxygen radical production by human neutrophils: possible mechanism(s) involved in its anti-inflammatory effect. Br J Pharmacol. 2002 January; 135(2):399-406). Andrographolide is known to inhibit the activity of NF-κB by interfering with the binding of NF-κB to DNA (Hidalgo M A, Romero A, Figueroa J, Cortes P, Concha I I, Hancke J L, Burgos R A. Andrographolide interferes with binding to nuclear factor-κB to DNA in HL-60-derived neutrophilic cells. Br J Pharmacol. 2005 March; 144(5):680-6).

In various embodiment of the present invention detailed in examples 1 and 2 below, the nutritional supplement comprises an extract of *Andrographis paniculata*. The amount of *Andrographis paniculata* extract in a serving of the nutritional supplement is from about 0.05 g to about 1 g. The preferred amount of *Andrographis paniculata* extract in a serving of the nutritional supplement is about 0.1 g.

In additional embodiments, the present invention may also include additional components known to attenuate NF-κB-mediated signaling to promote the efficacy of the composition. For example, the nutritional supplement may further comprise Diferuloylmethane (Curcumin) (Singh S, Aggarwal B B. Activation of transcription factor NF-kappa B is suppressed by curcumin (diferuloylmethane) [corrected] J Biol Chem. 1995 Oct. 20; 270(42):24995-5000. Erratum in: J Biol Chem 1995 Dec. 15; 270(50):30235) or Ethyl pyruvate (Pyruvic Acid Ethyl Ester) (Das U N. Pyruvate is an endogenous anti-inflammatory and anti-oxidant molecule. Med Sci Monit. 2006 May; 12(5):RA79-84). Ethyl pyruvate also has the benefit of providing an energy substrate beta-oxidation in the mit γ-butyrobetaine γ-butyrobetaine is an intermediate in carnitine biosynthesis in mammals. It is synthesized, from trimethyl lysine, in almost all cell types and then excreted into the blood to be reabsorbed by the kidney and liver. After reabsorption, γ-butyrobetaine is converted to carnitine by γ-butyrobetaine dioxygenase. This conversion to carnitine is extremely efficient, thus presence of γ-butyrobetaine in urine is very small (Vaz F M, Wanders R J A. Carnitine biosynthesis in mammals. Biochem J. 2002; 361:417-429).

The administration of γ-butyrobetaine to rats (Sjakste N, Kleschyov J L, Baumane L, Dzintare M, Meirena D, Sjakste J, Sydow K, Munzel T, Kalvinsh I. Endothelium- and nitric oxide-dependent vasorelaxing activities of gamma-butyrobetaine esters: possible link to the antiischemic activities of mildronate. Eur J Pharmacol. 2004 Jul. 8; 495(1):67-73 (Abstract)), provides vasodilating activities. These vasodilating activities were attributed to increases in nitric oxide concentrations in blood.

In various embodiment of the present invention detailed in examples 1 and 2 below, the nutritional supplement comprises γ-butyrobetaine or derivatives thereof. The amount of γ-butyrobetaine or derivatives thereof in a serving of the nutritional supplement is from about 0.01 g to about 1 g. The preferred amount of γ-butyrobetaine or derivatives thereof in a serving of the nutritional supplement is about 0.2 g.

Not wishing to be bound by theory, it is believed that the components of the present invention will act synergistically and simultaneously to promote improved protein metabolism in skeletal muscles. The BCAAs or derivatives thereof will act to increase skeletal muscle protein synthesis while decreasing skeletal muscle protein breakdown; the *Andrographis paniculata* extract and other like-directed components will act to attenuate inflammatory signals mediated by NF-κB resulting from intense exercise; the of γ-butyrobetaine or derivatives thereof will act to vasodilate blood vessels via increase nitric oxide to facilitate the delivery of nutrients to active or recovering skeletal muscles.

According to various embodiments of the present invention, the nutritional supplement may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage form of the present invention is a caplet.

Furthermore, the dosage form of the nutritional supplement may be provided in accordance with customary processing techniques for herbal and nutritional supplements in any of the forms mentioned above. Additionally, the nutritional supplement set forth in the example embodiment herein may contain any appropriate number and type of excipients, as is well known in the art.

The inclusion of specific excipients, as well as specific dosage formats may be utilized to achieve specific controlled-release of active ingredients. Such formats include but are not limited to quick-release, timed-release, slow-release and delayed-release.

The present nutritional composition or those similarly envisioned by one of skill in the art, may be utilized in methods to improve skeletal muscle protein synthesis. As such, the present invention may be utilized as a sole means of improving skeletal muscle protein synthesis or in combination with other like-directed compounds.

Although the following examples illustrate the practice of the present invention in two of its embodiments, the examples should not be construed as limiting the scope of the invention. Other embodiments will be apparent to one of skill in the art from consideration of the specifications and examples.

EXAMPLES

Example 1

A nutritional supplement in the form of caplets to be consumed twice daily. On workout days, one serving is to be taken 45 minutes before exercise and the second serving to be taken 30 minutes after exercise. On non-workout days, one serving is to be taken in the morning and the second serving to be taken in the afternoon. One serving of the nutritional supplement contains the following:

about 1.75 g L-Leucine, about 0.001 g L-Leucine Ethyl Ester HCL, about 0.001 g N-Acetyl L-Leucine, about 0.93 g L-Valine, about 0.001 g L-Valine Ethyl Ester, about 0.001 g N-Acetyl L-Valine, about 0.77 g L-Isoleucine, about 0.001 g L-Isoleucine Ethyl Ester, about 0.001 g N-Acetyl L-Isoleucine, about 0.25 g Diferuloylmethane, about 0.10 g Andrographis paniculata extract (15% Andrographolide), and about 0.05 g Pyruvic Acid Ethyl Ester (ethyl pyruvate).

Example 2

A nutritional supplement in the form of caplets to be consumed twice daily. On workout days, one serving is to be taken 45 minutes before exercise and the second serving to be taken 30 minutes after exercise. On non-workout days, one serving is to be taken in the morning and the second serving to be taken in the afternoon. One serving of the nutritional supplement contains the following:

about 3.55 g L-Leucine, about 0.001 g L-Leucine Ethyl Ester HCL, about 0.001 g N-Acetyl L-Leucine, about 1.85 g L-Valine, about 0.001 g L-Valine Ethyl Ester, about 0.001 g N-Acetyl L-Valine, about 1.54 g L-Isoleucine, about 0.001 g L-Isoleucine Ethyl Ester, about 0.001 g N-Acetyl L-Isoleucine, about 0.25 g Diferuloylmethane, about 0.10 g Andrographis paniculata extract, and about 0.05 g Pyruvic Acid Ethyl Ester (ethyl pyruvate).

Extensions and Alternatives

In the foregoing specification, the invention has been described with a specific embodiment thereof, however, it will be evident that various modifications and changes may be made thereto without departing from the broader spirit and scope of the invention.

What is claimed:

1. A method of improving skeletal muscle protein metabolism comprising administering an effective amount of a nutritional composition to a subject in need thereof, the composition comprising
    one or more branched-chain amino acids,
    an extract of *Andrographis paniculata*, and
    γ-butyrobetaine.

2. The method of claim 1, wherein the improving skeletal muscle protein metabolism comprises encouraging skeletal muscle protein synthesis and minimizing skeletal muscle protein breakdown.

3. The method of claim 2, wherein the nutritional composition further comprises an effective amount of ethyl pyruvate.

4. The method of claim 2, wherein the nutritional composition further comprises an effective amount of diferuloylmethane.

5. The method of claim 2, further comprising the steps of:
    administering a first serving of the nutritional composition about 45 minutes before exercise; and
    administering a second serving of the nutritional composition about 30 minutes after exercise.

6. The method of claim 3, wherein the nutritional composition further comprises an effective amount of diferuloylmethane.

7. A method of improving the skeletal muscle protein metabolism comprising administering an effective amount of a nutritional composition to a subject in need thereof, the composition comprising
    about 1.75 g L-Leucine,
    about 0.93 g L-Valine,
    about 0.77 g L-Isoleucine,
    about 0.10 g *Andrographis paniculata* extract (15% Andrographolide),
    about 0.2 g γ-butyrobetaine, and
    about 0.25 g Diferuloylmethane.

8. A method of improving the skeletal muscle protein metabolism comprising administering an effective amount of the nutritional composition to a subject in need thereof, the composition comprising
    about 1.75 g L-Leucine,
    about 0.93 g L-Valine,
    about 0.77 g L-Isoleucine,
    about 0.10 g *Andrographis paniculata* extract (15% Andrographolide),
    about 0.2 g γ-butyrobetaine, and
    about 0.05 g ethyl pyruvate.

* * * * *